United States Patent [19]

Hallberg et al.

[11] Patent Number: 5,028,398
[45] Date of Patent: Jul. 2, 1991

[54] DEVICE FOR PROVIDING A CONTINUOUS BIOLOGICAL DECOMPOSITION OF MINERALS AND CONCENTRATES THEREOF

[76] Inventors: Rolf O. Hallberg, Skolvägen 11 A, S-135 55 Tyresö; Ulf Edvardsson, Saimagatan 19, S-163 23 Spanga, both of Sweden

[21] Appl. No.: 327,188
[22] PCT Filed: Jul. 6, 1988
[86] PCT No.: PCT/SE88/00371
  § 371 Date: Apr. 21, 1989
  § 102(e) Date: Apr. 21, 1989
[87] PCT Pub. No.: WO89/00611
  PCT Pub. Date: Jan. 26, 1989

[30] Foreign Application Priority Data

Jul. 10, 1987 [SE] Sweden .................................. 8702836

[51] Int. Cl.⁵ .......................... B01J 8/00; C12M 1/00; B02C 25/00
[52] U.S. Cl. ............................ 422/189; 422/188; 422/190; 422/191; 435/303; 435/306; 435/313
[58] Field of Search ............... 422/193, 192, 191, 190, 422/189, 136, 145; 435/306, 308, 300, 288, 312, 313, 314, 315, 316; 366/220, 228, 230, 225, 227, 51; 51/422, 22

[56] References Cited

U.S. PATENT DOCUMENTS 4,223,094 9/1980 Vaseen .................................. 435/312
4,255,058 3/1981 Peleschka et al. .................... 366/25
4,480,922 11/1984 Mendenhall .......................... 366/25

Primary Examiner—David L. Lacey
Assistant Examiner—William K. Y. Chan
Attorney, Agent, or Firm—Pollock, Vande Sande & Priddy

[57] ABSTRACT

A lying rotatable drum for continuous biological decomposition which includes at least one transversal partition for dividing the container interior into chambers. The partition has opening to transmit liquid between the chambers. Guide means are also provided.

2 Claims, 1 Drawing Sheet

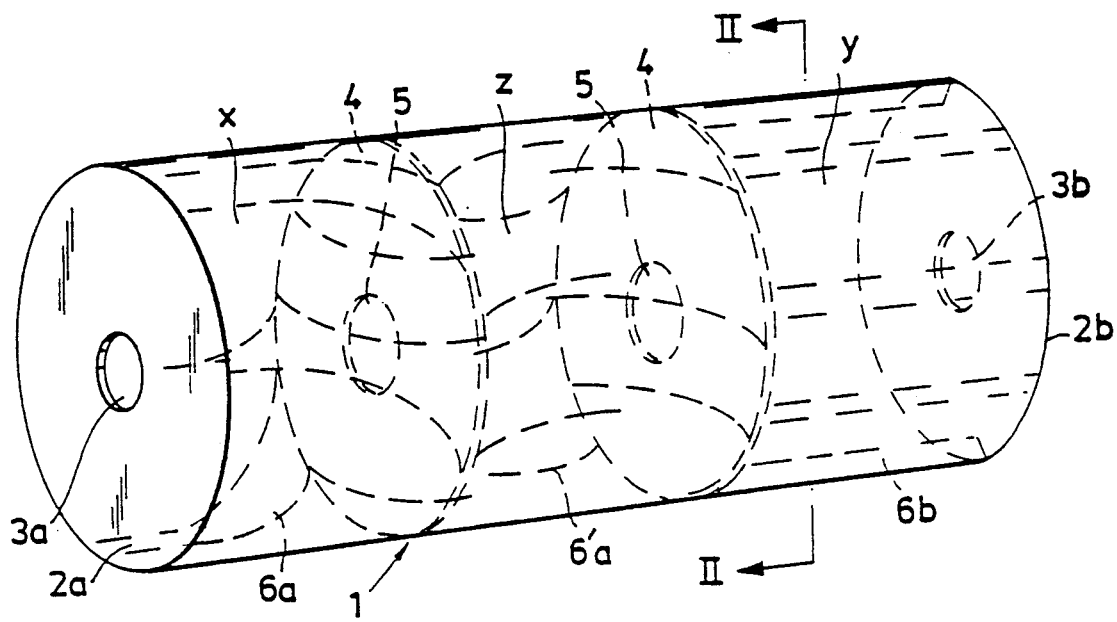
Fig. 2
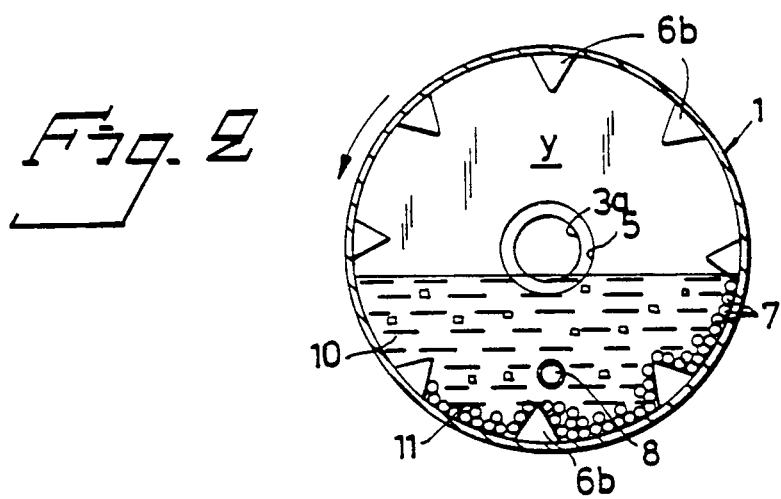
Fig. 3
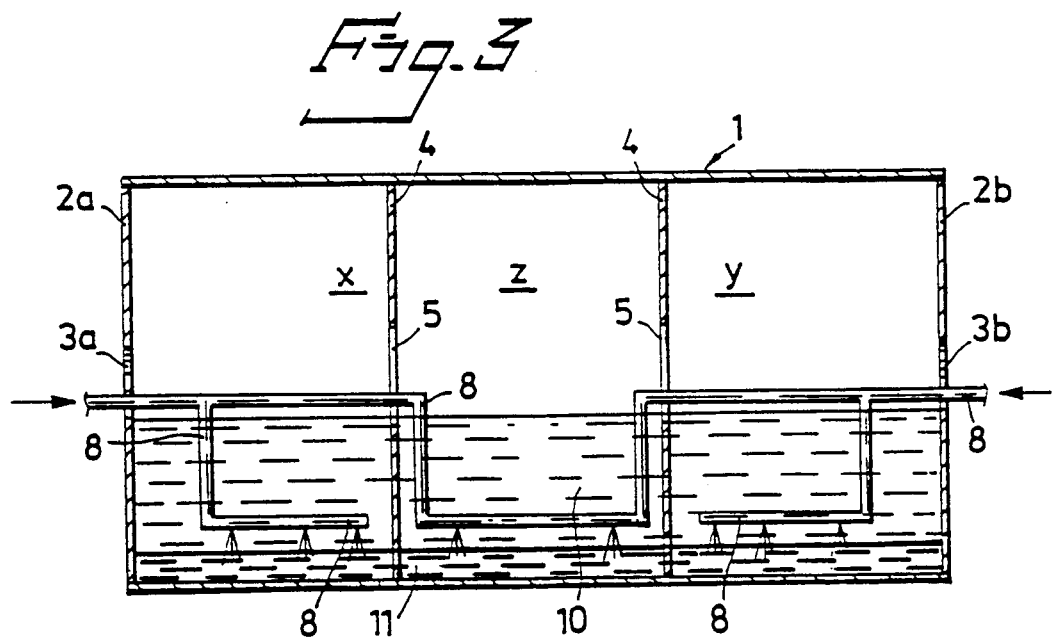

DEVICE FOR PROVIDING A CONTINUOUS BIOLOGICAL DECOMPOSITION OF MINERALS AND CONCENTRATES THEREOF

The invention refers to a device for providing a continuous biological decomposition of minerals and concentrates thereof by means of aerobic micro-organisms and comprising a lying elongated rotatable container with inlets and outlets at the ends thereof for mineral and nutrition solutions and bacteria and gas, internal guide means for circulation and oxygenization of the liquid mixture in the container and a drive device for rotating the container.

Biological decomposition of mostly sulfide minerals has been used for a long time as a method for obtaining metals from ores. Various methods have been developed for utilizing various parts of the ore. As example it might be mentioned that metal-poor wall rock from open pits is dumped into huge waste heaps, after which said heaps are sprayed with a solution containing a micro-organisms. From the leach solution obtained at the bottom the metals then are recovered.

For a ground ore or a mineral concentrate from ore usually various types of leach tanks are used. In said reacting tanks mineral concentrate, micro-organisms and nutrition solution are mixed and the metals then are recovered from the leach solution obtained. Attempts also have been made to connect several leach tanks with each other into a continuous system. In such case the mineral suspension has been pumped between the tanks in a constant flow or the flow between the tanks has been obtained by overflow from one tank to another.

There are mainly two types of leach tanks which are present, namely the so-called "Pachucha" tank and a stirred reactor tank. In a continuous system both said types are fed with a pulp consisting of a slurry of water and mineral concentrate. The biological decomposition then occurs in the tanks. The slurry is prepared in a separate storage tank. As far as the "Pachucha" tank is concerned, a strong air flow from below is used for addition of oxygen to the leach solution as well as for stirring so that the mineral particles do not settle. In the other type of reactor tank there is a mechanical agitator and the addition of oxygen usually occurs by introduction of air close to said agitator.

The capacity of both types of tanks is limited by the efficiency of the stirring. Particularly in continuous systems there is required a homogeneous slurry in order to avoid settling and hence an accumulation of solid material in the tanks. In its turn, this limits the range of particle distribution and the pulp density. Too high pulp density also might have toxical effects on the organisms.

Therefore, further development of the continuous system has resulted in a new type of tank, a lying rotatable drum. In principle, such a drum is known from U.S. Pat. No. 4,223,094 but the drum now suggested differs essentially from the known structure concerning feeding and discharging as well as the internal design. Furthermore also the way of working and the purpose differ essentially between the drums as well as the aeration of the solution.

The device according to the present invention is substantially distinguished by at least one transversal partition within the container at a position between the ends thereof for dividing the container interior into chambers, said partition having a central opening for transmission of the liquid mixture between the chambers, and in that the guide means are formed as profiles, mounted on and protruding radially inwardly from the inner wall of the container, which profiles in the chamber closest to the outlet end of the container extend parallel to each other and to the longitudinal axis of the container, while profiles in the chamber adjacent to the inlet end of the container from an orientation parallel to the longitudinal axis of the container at the container end are progressively curved towards the partition, and air supply means furthermore being mounted in each of the chambers.

The inventive device is particularly well suited for treatment of goldbearing arsenopyrite/pyrite concentrates as well as for leaching precious and rare earth metals and bulk concentrates of refractory ores.

By way of example, the invention will be further described below with reference to the accompanying drawing in which:

FIG. 1 is a diagrammatic perspective view in principle of a container according to the invention, FIG. 2 is a cross section through the container taken along the line II—II in FIG. 1, and FIG. 3 is a longitudinal section of the container.

As is illustrated in the drawing, the device according to the invention comprises a lying rotatable drum 1, adapted for continuous biological decomposition of mineral concentrate by means of aerobic micro-organisms. The drum 1 is tubular and closed at the ends by plates 2a, 2b, which either are attached to the drum 1 or stationary, such that the drum 1 rotates relative said plates. The feeding and discharging of material and bacteria and the solutions incorporated in the slurry 10 occurs through openings 3a, 3b in said end plates 2a, 2b (FIG. 1). In the first-mentioned case the openings 3a, 3b in the end plates 2a, 2b must be centrally located. In the latter case when the end plates 2a, 2b thus are stationary when the drum rotates, the openings 3a, 3b do not need to lie in the center but can be located as desired. The location and size of the openings 3a, 3b is determining for the working volume in the drum 1. Contrary to the disclosure of U.S. Pat. No. A 4,223,094 the drum constitutes an entirely open system and the discharge occurs by overflow.

By means of one or more partitions 4 secured to the drum 1, the same is divided into at least two sections or chambers x, y. The transport of material between said sections occurs through a centrally located opening 5 in the partition 4. The size of the opening controls the quantity of material transported between the sections x, y of the drum (FIG. 1).

In the sections x, y control means or so-called baffles 6a, 6b are mounted along the walls of the container. In the first section x as seen in the direction of flow, the feeding side, which forms a mixing chamber, said baffles have helical shape with progressively increased curvature such that the settled material is returned towards the end wall 2a. Closest to said end wall 2a, however, the baffles 6a are parallel, so that added grinding bodies 7 will assist in providing a mechanical decomposition (FIG. 1). Contrary to the "Pachucha" tank and the stirred reactor tank the drum 1 has no difficulties in coping with a certain sedimentation and therefore a wide range of particle sizes does not imply any limitations. Furthermore the average pulp density might be higher than in the two aforementioned known tank types since a slow rotation of the drum (<15 rpm) with a high pulp density implies that a portion of the heavier fractions will settle which reduces the risk of a toxical effect on the organisms (FIG. 2). It is this portion 11 of the solid material which then is treated by means of the added grinding bodies 7.

In the last section y at the discharge side, which is a reaction chamber, all baffles 6b are parallel over the entire length in order not to restrict the transport towards the discharge opening 3b, but at the same time, they have to assist in the continued mechanical decomposition by means of grinding bodies 7. By a further partition 4, an intermediate section z can be formed as seen in FIGS. 1 and 3, which also forms a reaction chamber and has oppositely helically curved baffles 6a in order to increase the mixing and to contribute to the mechanical decomposition by means of added grinding bodies.

The required supply of oxygen to the tank is made by pumping air into the solution through the baffles or through tubes 8 submerged in the solution and introduced through the openings 3a, 3b in the end plates 2a, 2b (FIG. 3).

We claim:

1. In a device for providing a continuous biological decomposition of minerals and concentrates thereof by means of aerobic micro-organisms and comprising a lying elongated rotatable container (1) with inlets and outlets (3a, 3b, respectively) at ends thereof for mineral and nutrition solutions and bacteria and gas, internal guide means (6a, 6b) for circulation and oxygenization of a liquid mixture in the container and a drive device for rotating the container, the improvement comprising at least one transversal partition (4) within the container (1) at a position between the ends thereof so as to divide the container interior into at least two chambers, said partition (4) having a central opening (5) for transmission of the liquid mixture between the chambers, and in that the guide means are formed as profiles (6a, 6b), mounted on and protruding radially inwardly from the inner wall of the container, which profiles in the chamber (y) closest to the outlet end of the container extend parallel to each other and to the longitudinal axis of the container, while the profiles in the chamber (x) adjacent to the inlet end of the container from an orientation parallel to the longitudinal axis of the container at the container inlet end are progressively curved towards the partition, and air supply means (8) furthermore being mounted in each of the chambers (x, y, z).

2. A device according to claim 1 wherein said at least one transversal partition comprises at least two transversal partitions forming at least one intermediate chamber (z), wherein the guide profiles in said intermediate chamber (z) have progressive helical curvature directed towards said inlet end.

* * * * *